United States Patent
Knoefler et al.

(10) Patent No.: US 10,627,382 B2
(45) Date of Patent: Apr. 21, 2020

(54) METHOD FOR CHECKING THE FUNCTIONAL CAPABILITY OF A NITROGEN OXIDE SENSOR

(71) Applicant: Robert Bosch GmbH, Stuttgart (DE)

(72) Inventors: Eckehard Knoefler, Marbach (DE); Torsten Handler, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 121 days.

(21) Appl. No.: 15/872,084

(22) Filed: Jan. 16, 2018

(65) Prior Publication Data
US 2018/0202986 A1  Jul. 19, 2018

(30) Foreign Application Priority Data
Jan. 16, 2017  (DE) .................. 10 2017 200 549

(51) Int. Cl.
*G01N 27/416* (2006.01)
*G01N 33/00* (2006.01)
*F01N 11/00* (2006.01)

(52) U.S. Cl.
CPC .......... *G01N 33/007* (2013.01); *F01N 11/00* (2013.01); *F01N 11/007* (2013.01); *G01N 33/0037* (2013.01); *F01N 2560/026* (2013.01); *F01N 2560/12* (2013.01); *Y02A 50/245* (2018.01); *Y02T 10/47* (2013.01)

(58) Field of Classification Search
CPC ............. G01N 27/4175; G01N 27/419; G01N 27/4074; G01N 33/0037; Y02A 50/245; F01N 2550/02; F01N 2560/026; F01N 11/00; F01N 2550/00; Y02T 10/47
See application file for complete search history.

(56) References Cited

U.S. PATENT DOCUMENTS

| 6,344,134 B1* | 2/2002 | Yamada ............... G01N 27/417 204/425 |
| 2005/0061684 A1 | 3/2005 | Bausewein et al. |
| 2008/0011051 A1* | 1/2008 | Lemire ............... G01N 27/419 73/23.31 |
| 2012/0097553 A1* | 4/2012 | Classen .............. G01N 27/4074 205/781 |
| 2015/0377822 A1* | 12/2015 | Yoshida ............... G01N 27/419 205/784 |
| 2019/0195828 A1* | 6/2019 | Knoefler ............... F01N 11/007 |

FOREIGN PATENT DOCUMENTS

DE  10312732  10/2004

OTHER PUBLICATIONS

Kato, N. et al., "Thick Film ZrO2 NOx Sensor," Technical Paper 960334, 1996.

* cited by examiner

*Primary Examiner* — Brandi N Hopkins
(74) *Attorney, Agent, or Firm* — Michael Best & Friedrich LLP

(57) ABSTRACT

A method is presented for checking the functional capability of a nitrogen oxide sensor (10) which has a first chamber (12) and a second chamber (14), wherein the first chamber has a first oxygen pump cell (20) and the second chamber has a second pump cell (34), in a normal operating mode of the nitrogen oxide sensor (10), an oxygen concentration level in the first chamber is reduced to a predetermined first value with the first pump cell, and an oxygen concentration level in the second chamber is reduced to a second value with the second pump cell, said second value being lower than the first value.

14 Claims, 2 Drawing Sheets

METHOD FOR CHECKING THE FUNCTIONAL CAPABILITY OF A NITROGEN OXIDE SENSOR

BACKGROUND OF THE INVENTION

The present invention relates to a method for checking the functional capability of a nitrogen oxide sensor. Such a method is known, for example, from DE 103 12 732 B4. With regard to its device aspects, the invention relates to a control unit.

Nitrogen oxide sensors are known, for example, from document SAE 960334 "Thick Film ZrO2 NOx Sensor". Such sensors have a first chamber and a second chamber, wherein the first chamber is connected to a measuring gas space via a first diffusion barrier. A diffusion barrier is here, for example, a porous structure which impedes a diffusion of gas particles without, however, completely blocking them. The measuring gas is, for example, the exhaust gas of an internal combustion engine. The first chamber has a first oxygen pump cell which is electrically connected to a control unit. The second chamber is connected to the first chamber via a second diffusion barrier and has a second pump cell which is electrically connected to the control unit. In a normal operating mode of the nitrogen oxide sensor, an oxide concentration level in the first chamber is reduced to a predetermined first value with the first pump cell. An oxygen concentration level which occurs in the second chamber is reduced to a second value with the second pump cell by releasing oxygen from the nitrogen oxides, said second value being lower than the first value. The pump flow which occurs here in the solid electrolyte of the second pump cell and therefore in the second pump cell is essentially carried by oxygen ions which result from the decomposition of nitrogen oxides. This pump flow is therefore a measure of the nitrogen oxide concentration in the exhaust gas.

SUMMARY OF THE INVENTION

According to these features, in the method there is provision that in a diagnostic mode of the nitrogen oxide sensor the oxygen concentration level in the first chamber is set to an increased value, that a change, occurring in reaction thereto, in a pump flow which flows in the second pump cell is detected, and the change or a variable derived from the change is compared with a value range of permitted values, which is valid for a functionally capable nitrogen oxide sensor, and the nitrogen oxide sensor is assessed as faulty if the change or the variable derived therefrom lies outside the value range.

It has become apparent that with this method it is possible to differentiate reliably between still good NOx sensors in terms of NOx signal dynamics and NOx sensors which are already no longer sufficiently functionally capable. Therefore, an advantageous alternative to the previously known methods for monitoring the dynamics of an NOx signal is made available. The previous methods compare the NOx signal dynamics with a model which is calculated from engine parameters. In applications behind NOx reduction catalytic converters such as NSC or SCR on the one hand a sufficient excitation is no longer present owing to reduced nitrogen oxide emissions, and, on the other hand, sufficiently precise modelling of the NOx emissions is no longer possible.

Setting the oxygen concentration level present in the first chamber to an increased value also causes more oxygen to flow from the first chamber into the second chamber via the second diffusion barrier. As a consequence, the pump flow flowing in the second pump cell is increased. The time behavior of this change depends on the state of the components which are involved in the transportation of gas particles from the measuring gas into the solid electrolyte of the second pump cell.

It is, for example, possible for the second diffusion barrier to become entirely or partially blocked, or for the electrode of the second pump cell to become catalytically inactive, e.g. owing to poisoning. This results in an increased resistance for the flow of oxygen, which reduces the speed and the degree to which the change, occurring in the first chamber, in the oxygen concentration level in the pump flow signal of the second pump cell is modelled.

Conversely, it is, for example, also possible for the diffusion resistance of the second diffusion power and/or an electrode of the second pump cell to be reduced by damage, for example by a fracture. This results in reduced resistance for the flow of oxygen, which increases the speed and the degree to which the change, occurring in the first chamber, in the oxygen concentration level in the pump flow signal of the second pump cell in comparison with the sensor in its new state.

It has become apparent that the comparison with the value range constitutes a reliable criterion with which still sufficiently functionally capable sensors can be differentiated from no longer sufficiently functionally capable sensors.

A preferred refinement is distinguished by the fact that a gradient of the rise in the pump flow flowing in the second pump cell is ascertained as the variable derived from the change.

It is also preferred that the range of permitted values which is valid for a functionally capable nitrogen oxide sensor is the range of the product of the gradient with a factor 1−x as the lower limit up to the product of the gradient with a factor 1+y as the upper limit, wherein x and y are numbers between 0 and 1.

In addition it is preferred that x=y. Alternatively it is preferred that x is unequal to y.

It is also preferred that a value of the gradient of the pump flow profile is also ascertained at a transition from the diagnostic mode into the normal operating mode and is compared with a range of permitted values.

It is also preferred here that the range of permitted values for this case is ascertained in the same manner as the range of permitted values for the case of the transition from the normal operating mode into the diagnostic mode.

A further preferred refinement is distinguished by the fact that the nitrogen oxide sensor is evaluated as being faulty when the ascertained value for both directions does not lie in the range of permitted values, or if said value does not lie in the range of permitted values only at the transition from the normal operating mode into the diagnostic mode or only at the transition from the diagnostic mode into the normal operating mode.

It is also preferred that the value range which is valid for a functionally capable nitrogen oxide sensor is ascertained by virtue of the fact that the oxygen concentration level in the first chamber is set to a value which is increased in comparison with a normal operating mode of the nitrogen oxide sensor at the end of the production of the nitrogen oxide sensor or in the new state of the sensor when it is used in an exhaust gas system of an internal combustion engine, in that a change, occurring in reaction thereto, in a pump flow flowing in the second pump cell is detected, and the change or a variable derived from the change is stored as a basic value for a value range which characterizes a functionally capable nitrogen oxide sensor.

With regard to refinements of the control unit according to the invention, it is preferred that the latter is configured, in particular programmed, to control a sequence of a method according to the invention or of one of its refinements.

It is self-evident that the features which are mentioned above and the features which are still to be explained can be used not only in the respectively specified combination but also in other combinations or alone without departing from the scope of the present invention.

BRIEF DESCRIPTION OF THE DRAWINGS

Exemplary embodiments of the invention are illustrated in the drawings and are explained in more detail in the following description. In this context, identical reference symbols in various figures respectively denote elements which are identical or at least comparable in terms of their function. The figures in the drawings each denote, in a schematic form, the following.

DETAILED DESCRIPTION

Figure 1:
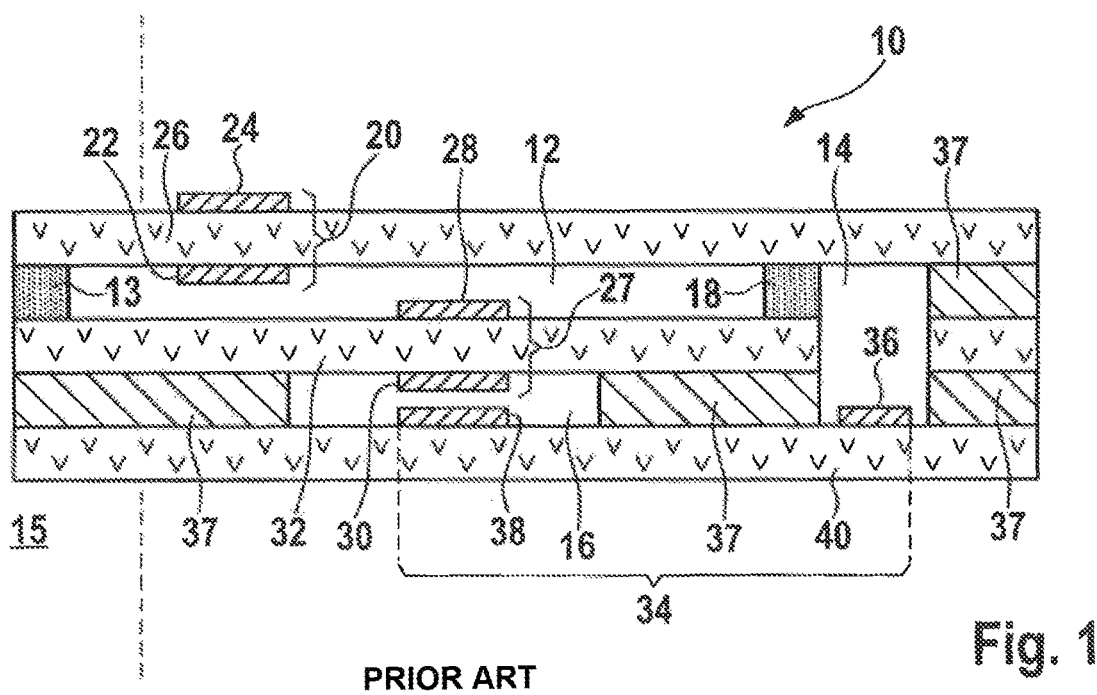
FIG. 1 shows a cross section through a known nitrogen oxide sensor.

In particular, FIG. 1 shows a cross section through a known nitrogen oxide sensor 10. The nitrogen oxide sensor 10 has a first chamber 12 and a second chamber 14 as well as a reference air duct 16. The first chamber 12 can be connected to the measuring gas space 15 via a first, porous diffusion barrier 13. The measuring gas space is e.g. an exhaust gas system of an internal combustion engine, and the connection is carried out by screwing the sensor to a wall of the exhaust gas system. The first diffusion barrier 13 then faces, with its side facing away from the first chamber 12, the exhaust gas of the internal combustion engine. The reference air duct 16 and the second chamber 14 are not connected to the measuring gas space 15 here. The reference air duct 16 leads into the ambient air. The second chamber 14 is connected to the first chamber 12 via a second, porous diffusion barrier 18. The first chamber 12 has a first oxygen pump cell 20, which is composed of a first inner pump electrode 22, a second outer pump electrode 24 and a solid electrolyte 26 which is located between these two pump electrodes and is suitable for conducting oxygen ions. The solid electrolyte is composed e.g. of zirconium dioxide. The electrodes respectively adhere fixedly to the solid electrolyte. This also applies to other pump cells and measuring cells which are specified in this application. The first chamber 12 also has a measuring cell 27 which is composed of a first inner measuring electrode 28 facing the interior of the first chamber 12, a first outer measuring electrode 30 facing the reference air duct 16, and a solid electrolyte 32 which lies between these two electrodes.

The second chamber 14 has a second oxygen pump cell 34 which is composed of a third inner pump electrode 36 facing the interior of the second chamber 14, an outer fourth pump electrode 38 facing the interior of the reference air duct, and a solid electrolyte 40 lying between these two electrodes. The regions 37 are composed of a non-metallic carrier material which does not have any ion conductivity.

Figure 2:
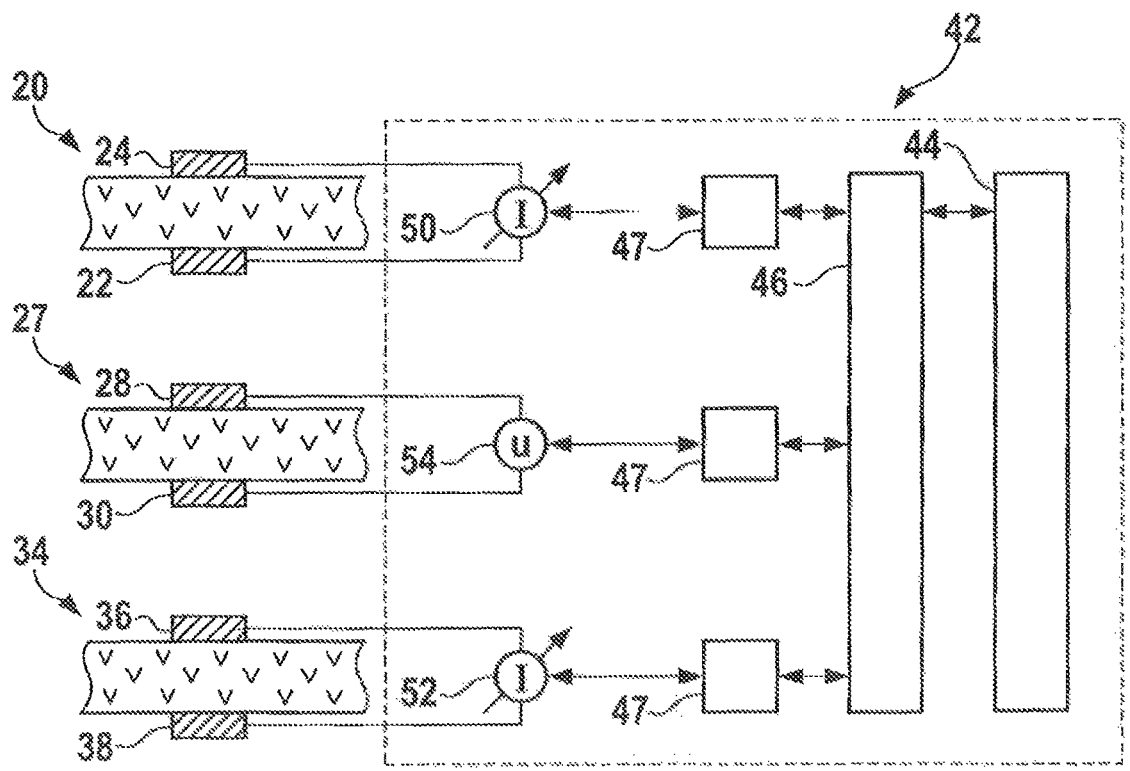
FIG. 2 shows two pump cells and a measuring cell of the known nitrogen oxide sensor together with a control unit which is electrically connected to each of the specified cells.

FIG. 2 shows the two pump cells 20 and 34 and the measuring cell 27 together with a control unit 42 which is electrically connected to each of the specified cells 24, 34 and 27. The control unit 42 has an accumulator 44, a processor 46 and interface modules 47 which prepare input signals and output signals. Furthermore, the control unit has a first controllable pump voltage source 50, a second controllable pump voltage source 52 and a voltage measuring unit 54, for example an analog/digital converter 55. The voltage measuring unit 54 detects the voltage which is produced between the electrodes 28 and 30 of the measuring cell 27 and which is a measure of the oxygen concentration level in the first chamber 12.

The control unit 42 actuates the pump voltage source 50 as a function of this voltage and in accordance with a program which is stored in the memory 44, in such a way that a predefined, very low oxygen concentration level is set in the first chamber 12. The normal operating mode is the mode in which the nitrogen oxide sensor 10 detects the nitrogen oxide concentration level in the measuring gas.

The pump voltage source 52 of the second pump cell 34 is operated in the normal operating mode in such a way that it pumps away virtually all the nitrogen oxides flowing in via the second diffusion barrier 18. This occurs by releasing the oxygen which is initially still bound to nitrogen oxides. The strength of the resulting pump flow here forms the nitrogen oxide concentration level of the measuring gas in the normal operating mode.

Figure 3:
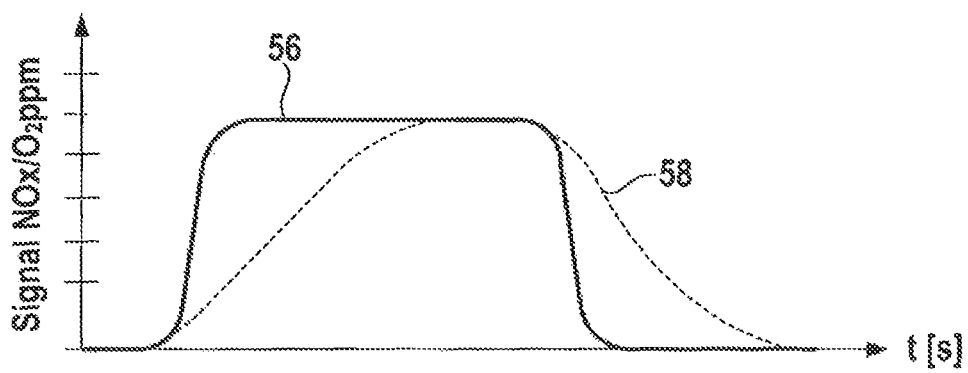
FIG. 3 shows profiles of the pump flow of the second pump cell plotted against the time at the transition from the normal operating mode into a diagnostic mode, and at the return into the normal operating mode for the case of a new nitrogen oxide sensor and for the case of an aged nitrogen oxide sensor.

FIG. 3 shows profiles of the pump flow and the second pump cell 34 plotted against the time at the transition from the normal operating mode into a diagnostic mode, and at the return into the normal operating mode for the case of a new nitrogen oxide sensor and for the case of an aged nitrogen oxide sensor. Here, the nitrogen oxide concentration level which is modelled in the pump flow is plotted in the second chamber in ppm against the time t in s. The profile 56 is obtained with a new nitrogen oxide sensor 10. Up to the time t0, the nitrogen oxide sensor 10 is operated in the normal operating mode. In this context, the setpoint value of the Nernst voltage which is detected with the measuring cell 27 is e.g. 425 mV or another normal operating value. At the time t0 the setpoint value is lowered to e.g. 225 mV or some other diagnostic operating value.

It is essential that the diagnostic operating value is less than the normal operating value. As a result, an increased oxygen concentration level is set in the first chamber because less oxygen is pumped away. As a further result, more oxygen then flows into the second chamber via the second diffusion barrier. Subsequently, the second pump flow which is pumped out of the second chamber using the second pump cell increases. The change in the setpoint value in the first pump cell gives rise e.g. to an average oxygen concentration of 300 ppm in the second chamber. This value is then composed of the offset caused by additional oxygen in the second pump cell from the change in the change in the setpoint value of the first pump cell.

In this context, the curve 56 has a large gradient. The curve 58, which has a relatively small gradient, is obtained for the case of an aged sensor, which has an increased flow resistance of the second diffusion barrier or a blocked electrode.

In one preferred refinement, a gradient of the rise in the pump flow signal, such as occurs at the described transition from the normal operating mode into the diagnostic mode, is ascertained and compared with a range of permitted values which characterize a still functionally capable nitrogen oxide sensor 10.

Such a range is preferably acquired by virtue of the fact that the described method is carried out in order to ascertain the gradient in the production at the end of the belt, and the value which is obtained here is used as an average gradient value m of the range of permitted values for values which are ascertained during later operation of the nitrogen oxide sensor. In one preferred refinement, the range of permitted values is the range from $(1-x)m$ to $(1+y)m$, wherein x and y are preferably numbers between 0.1 and 0.4. It is particularly preferred that $x=y=0.2$. The variable x can also be unequal to y.

It is also preferred that at the return into the normal operating mode a value of the gradient of the pump flow profile is determined and is compared with a range of permitted values. The range of permitted values is to be ascertained for this case precisely like the range of permitted values for the case of the transition from the normal operating mode into the diagnostic mode. The nitrogen oxide sensor is evaluated as being faulty when the ascertained value for both directions drops out of the range of permitted values or when it drops out of the range of permitted values only for one direction. A first direction occurs for the transition from the normal operating mode into the diagnostic mode. The second direction occurs for the transition from the diagnostic mode into the normal operating mode.

Figure 4:
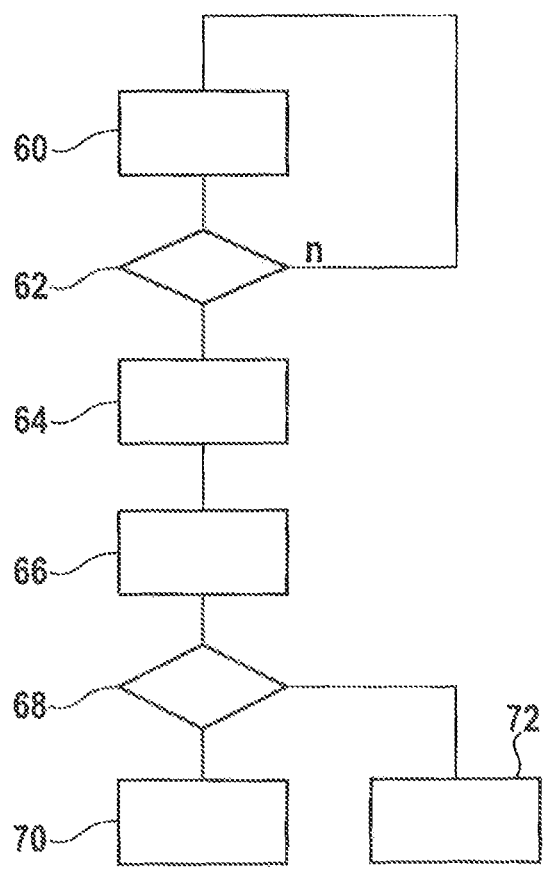
FIG. 4 shows a flowchart as an exemplary embodiment of a method according to the invention in which profiles occur such as are illustrated in FIG. 3.

FIG. 4 shows a flowchart of an exemplary embodiment of a method according to the invention in which profiles occur such as are illustrated in FIG. 3. The sequence of the method according to the invention is controlled by the control unit 42. The control unit 42 is configured, in particular programmed, to control the sequence of the method according to the invention and/or one of its refinements.

The step 60 then corresponds to the normal operating mode of the nitrogen oxide sensor 10. Here, the setpoint value for the Nernst voltage detected over the measuring cell 27 is e.g. 425 mV or another normal operating value. In step 62 it is checked whether diagnostics are to take place. If this is not the case, the program returns to the step 60. The loop from the steps 60 and 62 is exited when specific test conditions are present. These test conditions characterize e.g. a situation in which an internal combustion engine whose exhaust gas system is equipped with a nitrogen oxide sensor 10 is switched off in the operationally warm state. There are then sufficiently stable test conditions present, e.g. a constant exhaust gas composition in the exhaust gas system which then serves as a measuring gas space.

In this case, the step 62 is adjoined by a step 64 in which the first chamber 12 of the nitrogen oxide sensor is flooded with oxygen. The flooding of oxygen is preferably carried out by lowering the setpoint value of the Nernst voltage between the electrodes 28 and 30 of the measuring cell 27 to a value which is less than the setpoint value used in the normal operating mode. The lowered setpoint value is, for example, 225 mV.

Subsequently, in the step 66 the profile of the pump flow in the second chamber 14 is detected, and the pump flow itself or a variable based on values of the pump flow is compared with a range of permitted values. This comparison takes place in step 68. The variable which is based on values of the pump flow is preferably a gradient of the signal which models the pump flow and which occurs at the transition from the normal operating mode into the diagnostic mode and/or vice versa.

The range of permitted values is, as has been mentioned above, in one preferred refinement a range from $(1-x)m$ to $(1+y)m$, where x and y are preferably numbers between 0.1 and 0.4. It is particularly preferred that $x=y=0.2$. The variable x can also be unequal to y. It is also preferred that at the return into the normal operating mode a value of the gradient of the pump flow profile is also ascertained and compared with a range of permitted values. The range of permitted values is to be ascertained for this case precisely in the same way as the range of permitted values for the case of the transition from the normal operating mode into the diagnostic mode.

If the ascertained gradient m is in the range $(1-x)m$ to $(1-y)m$ of permitted values, the nitrogen oxide sensor in the step 70 is evaluated as being sufficiently functionally capable. Otherwise, in step 72 a fault message occurs which is displayed to the driver via a fault lamp and/or which is stored in the control unit for later use. In one refinement, the nitrogen oxide sensor is evaluated as being faulty if the ascertained value drops out of the range of permitted values only for one direction. In another refinement, said nitrogen oxide sensor is evaluated as being faulty when it drops out of the range of permitted values for both directions.

The invention claimed is:

1. A method for checking the functional capability of a nitrogen oxide sensor (10) which has a first chamber (12) and a second chamber (14), wherein the first chamber (12) is connected to a measuring gas space (15) via a first diffusion barrier (13) and has an oxygen pump cell (20) which is connected electrically to a control unit, and wherein the second chamber (14) is connected to the first chamber (12) via a second diffusion barrier (18) and has a second pump cell (34), and wherein in a normal operating mode of the nitrogen oxide sensor (10), an oxygen concentration level in the first chamber (12) is reduced to a predetermined first value with the first pump cell (20), and wherein an oxygen concentration level in the second chamber is reduced to a second value with the second pump cell (34) by releasing oxygen from the nitrogen oxides, said second value being lower than the first value, wherein in a diagnostic mode of the nitrogen oxide sensor (10) the oxygen concentration level in the first chamber (12) is set to an increased value, in that a change, occurring in reaction thereto, in a pump flow which flows in the second pump cell (34) is detected, and the change or a variable derived from the change is compared with a value range of permitted values, which is valid for a functionally capable nitrogen oxide sensor (10), and the nitrogen oxide sensor (10) is assessed as faulty if the change or the variable derived therefrom lies outside the value range, and a fault message is generated when the nitrogen oxide sensor (10) is determined to be faulty, wherein a gradient of an increase in the pump flow flowing in the second pump cell is ascertained as the variable derived from the change, and wherein the range of permitted values, which is valid for a functionally capable nitrogen oxide sensor, is the range of a product of the gradient with a factor 1-x as a lower limit up to a product of the gradient with a factor 1+y as an upper limit, wherein x and y are numbers between 0 and 1.

2. The method according to claim 1, wherein $x=y$.

3. The method according to claim 1, wherein x is unequal to y.

4. The method according to claim 1, wherein a value of the gradient of the pump flow profile is also ascertained at a transition from the diagnostic mode into the normal operating mode and is compared with a range of permitted values.

5. The method according to claim 4, wherein the range of permitted values is ascertained in the same manner as the range of permitted values for the case of the transition from the normal operating mode into the diagnostic mode.

6. The method according to claim 1, wherein the nitrogen oxide sensor is evaluated as being faulty if an ascertained value for both directions does not lie in the range of permitted values, or if said value does not lie in the range of permitted values only at the transition from the normal operating mode into the diagnostic mode or only at the transition from the diagnostic mode into the normal operating mode.

7. The method according to claim 1, wherein the value range which is valid for a functionally capable nitrogen oxide sensor (10) is ascertained by virtue that the oxygen concentration level in the first chamber (12) is set to a value which is increased in comparison with a normal operating mode of the nitrogen oxide sensor at an end of a production of the nitrogen oxide sensor or in a new state of the sensor when it is used in an exhaust gas system of an internal combustion engine, in that a change, occurring in reaction thereto, in a pump flow flowing in the second pump cell (34) is detected, and the change or a variable derived from the change is stored as a basic value for a value range which characterizes a functionally capable nitrogen oxide sensor (10).

8. A control unit (42) configured to check the functional capability of a nitrogen oxide sensor (10) which has a first chamber (12) and a second chamber (14), wherein the first chamber (12) is connected to a measuring gas space (15) via a first diffusion barrier (13), and has a first oxygen pump cell (20) which is electrically connected to the control unit, and wherein the second chamber (14) is connected to the first chamber (12) via a second diffusion barrier (18) and has a second pump cell (34), and wherein the control unit is configured to reduce, in a normal operating mode of the nitrogen oxide sensor (10), an oxygen concentration level in the first chamber (12) to a predetermined first value with the first pump cell (20), and to reduce an oxygen concentration level in the second chamber to a second value with the second pump cell (34) by releasing oxygen from the nitrogen oxides, said value being lower than the first value, wherein the control unit is configured to set, in a diagnostic mode of the nitrogen oxide sensor (10), the oxygen concentration level in the first chamber (12) to an increased value, to detect a change, occurring in reaction thereto, in a pump flow flowing in the second pump cell (34), and to compare the change or a variable derived from the change with a value range which is valid for a functionally capable nitrogen oxide sensor (10) and to assess the nitrogen oxide sensor (10) as faulty if the change or the variable derived therefrom lies outside the value range, wherein a gradient of an increase in the pump flow flowing in the second pump cell is ascertained as the variable derived from the change, and wherein the range of permitted values, which is valid for a functionally capable nitrogen oxide sensor, is the range of a product of the gradient with a factor 1-x as a lower limit up to a product of the gradient with a factor 1+y as an upper limit, wherein x and y are numbers between 0 and 1.

9. The control unit according to claim 8, wherein x=y.

10. The control unit according to claim 8, wherein x is unequal to y.

11. The control unit according to claim 8, wherein a value of a gradient of the pump flow profile is also ascertained at a transition from the diagnostic mode into the normal operating mode and is compared with a range of permitted values.

12. The control unit according to claim 8, wherein the range of permitted values is ascertained in the same manner as the range of permitted values for the case of the transition from the normal operating mode into the diagnostic mode.

13. The control unit according to claim 8, wherein the nitrogen oxide sensor is evaluated as being faulty if the ascertained value for both directions does not lie in the range of permitted values, or if said value does not lie in the range of permitted values only at the transition from the normal operating mode into the diagnostic mode or only at the transition from the diagnostic mode into the normal operating mode.

14. The control unit according to claim 8, wherein the value range which is valid for a functionally capable nitrogen oxide sensor (10) is ascertained by virtue that the oxygen concentration level in the first chamber (12) is set to a value which is increased in comparison with a normal operating mode of the nitrogen oxide sensor at the end of the production of the nitrogen oxide sensor or in the new state of the sensor when it is used in an exhaust gas system of an internal combustion engine, in that a change, occurring in reaction thereto, in a pump flow flowing in the second pump cell (34) is detected, and the change or a variable derived from the change is stored as a basic value for a value range which characterizes a functionally capable nitrogen oxide sensor (10).

* * * * *